United States Patent [19]

Hamamura et al.

[11] 4,433,159

[45] Feb. 21, 1984

[54] SYNTHESIS OF OPTICALLY ACTIVE D-ALPHA TOCOPHEROL

[75] Inventors: Kimio Hamamura, Kashiwa; Kozo Akasaka; Youji Yamagishi, both of Tokyo, all of Japan

[73] Assignee: Eisai Co., Ltd., Tokyo, Japan

[21] Appl. No.: 349,950

[22] Filed: Feb. 18, 1982

[30] Foreign Application Priority Data

Feb. 19, 1981 [JP] Japan ................................ 56-22212

[51] Int. Cl.$^3$ .................. C07D 311/72; C07D 303/14
[52] U.S. Cl. ................................ 549/411; 260/396 R; 549/529; 549/555; 568/592; 568/496; 568/853; 560/254; 560/262
[58] Field of Search .............................. 549/411, 529; 260/396 R; 568/766

[56] References Cited

U.S. PATENT DOCUMENTS

| | | | |
|---|---|---|---|
| 2,311,887 | 2/1943 | Tishler et al. | 549/411 |
| 3,080,384 | 3/1963 | Kofler et al. | 260/396 R |
| 3,360,584 | 12/1967 | Kollar | 549/529 |
| 3,455,959 | 7/1969 | Mayer et al. | 549/411 |
| 3,870,729 | 3/1975 | Bost et al. | 549/529 |
| 3,879,448 | 4/1975 | Morimoto et al. | 260/396 R |
| 4,061,660 | 12/1977 | Kijima et al. | 260/396 R |

*Primary Examiner*—Nicky Chan
*Attorney, Agent, or Firm*—Flynn, Thiel, Boutell & Tanis

[57] ABSTRACT

Optically active alpha-tocopherol is synthesized by a multi-step process using phytol as a starting material. The process does not require an optical resolution step.

8 Claims, No Drawings

SYNTHESIS OF OPTICALLY ACTIVE D-ALPHA TOCOPHEROL

This invention relates to a newly developed industrial method for the synthesis of optically active alpha-tocopherol.

The compound d-alpha-tocopherol is the principal compound present in natural vitamin E sources. At present, d-alpha-tocopherol and other tocopherol derivatives are used in pharmaceuticals, foods and animal feeds.

Because d-alpha-tocopherol must generally be extracted from natural sources, such as vegetable oils, it is not suitable for industrial mass production. The content of d-alpha-tocopherol in vegetable oils is very small, and it is essential to purify d-alpha-tocopherol by separating it from beta, gamma and delta tocopherol isomers.

Several attempts to synthesize optically active alpha-tocopherol have been reported; for instance, see H. Mayler and O. Isler et al Helv. Chim. Acta. 46, 650 (1963); J. W. Scott, W. M. Cort, H. Harley, F. T. Bizzarro, D. R. Panish and G. Saucy, J. Amer. Chem. Soc. 51, 200 (1974); ibid 52, 174 (1975); Helv. Chim. Acta. 59, 290 (1976); K. K. Chan, and N. Cohen et al, J. Org. Chem. 41, 3497, 3512 (1976); ibid 43, 3435 (1978). None of these methods are suitable for industrial mass production.

Known methods, including those cited above, require an optical resolution step, and this causes a serious reduction of the yield of about 30 to 40%. The present inventors have conducted extensive research in order to achieve a method of synthesis that does not require an optical resolution step, and have discovered the method of the present invention. The invention is described as follows.

In accordance with the present invention, a compound of the formula (I) is converted to a compound of the formula (XI) or (XI') via the following intermediates.

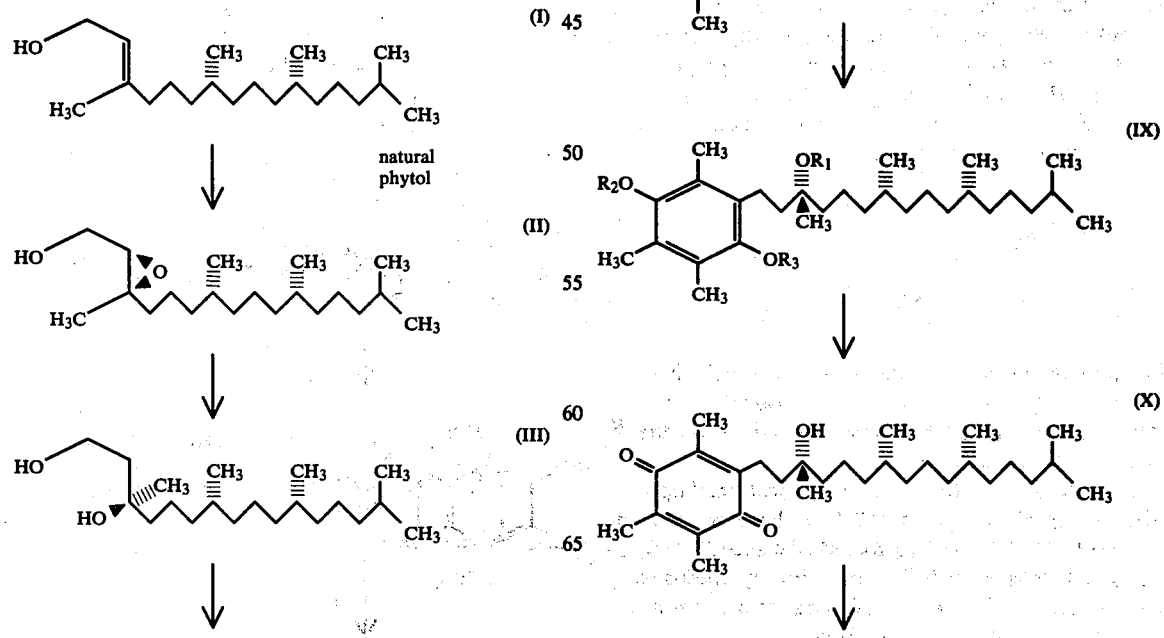

-continued

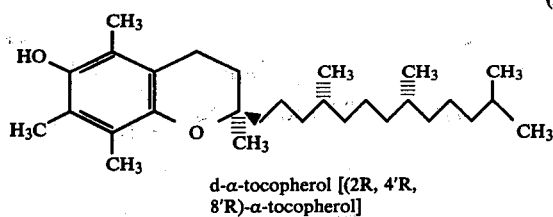

d-α-tocopherol [(2R, 4'R, 8'R)-α-tocopherol] (XI)

In the structural representations of the compounds given throughout this application, $R_1$, $R_2$, $R_3$ and $R_4$, which are the same or different, indicate protecting groups of the hydroxyl function, and X indicates halogen. A wedge-shaped line (▼) indicates a substituent which protrudes out of the plane of the paper towards the reader, that is, the particular substituent is above the overall plane of the molecule. A broken line (≡) indicates a substituent which protrudes out of the plane of the paper in the direction away from the reader, that is, the particular substituent is below the overall plane of the molecule. A wavy line (∫) indicates a mixture of two compounds, each of which has the substituent, but wherein the substituent is above the plane for one compound and below the plane for the other.

In accordance with this invention, natural d-alpha-tocopherol, namely (2R, 4'R, 8'R) alpha-tocopherol, is synthesized.

The detailed description of this invention is as follows.

The compound of formula (I) (natural phytol) is converted to the compound of formula (II) or (II') (see below) by enantio selective oxidation. This oxidation is carried out with natural phytol (I), diethyl tartrate, titanium tetraisopropoxide and t-butyl hydroperoxide, in a halogenated hydrocarbon solvent, such as dichloromethane, trichloroethane, etc., at a temperature in the range of −70° C. to 30° C. In carrying out this reaction, any tartrate ester can be utilized. Preferred tartrate esters include dimethyl tartrate and diethyl tartrate. If D-(−)-diethyl tartrate is utilized, then the compound of the formula (II) will be produced. If the L-(+)-diethyl tartrate is utilized, then the compound of the formula (II') given below will be produced.

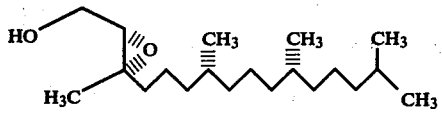
(II')

The compound of the formula (II') is ultimately converted to an optically active alpha-tocopherol compound, namely, (2S, 4'R, 8'R) alpha-tocopherol in the manner illustrated above.

In accordance with this invention, the term "optically active alpha-tocopherol" relates both to compounds of (2R, 4'R, 8'R)-alpha-tocopherol and (2S, 4'R, 8'R)-alpha-tocopherol. The process for synthesizing (2S, 4'R, 8'R) alpha-tocopherol starting from the compound of the formula (II') is as follows.

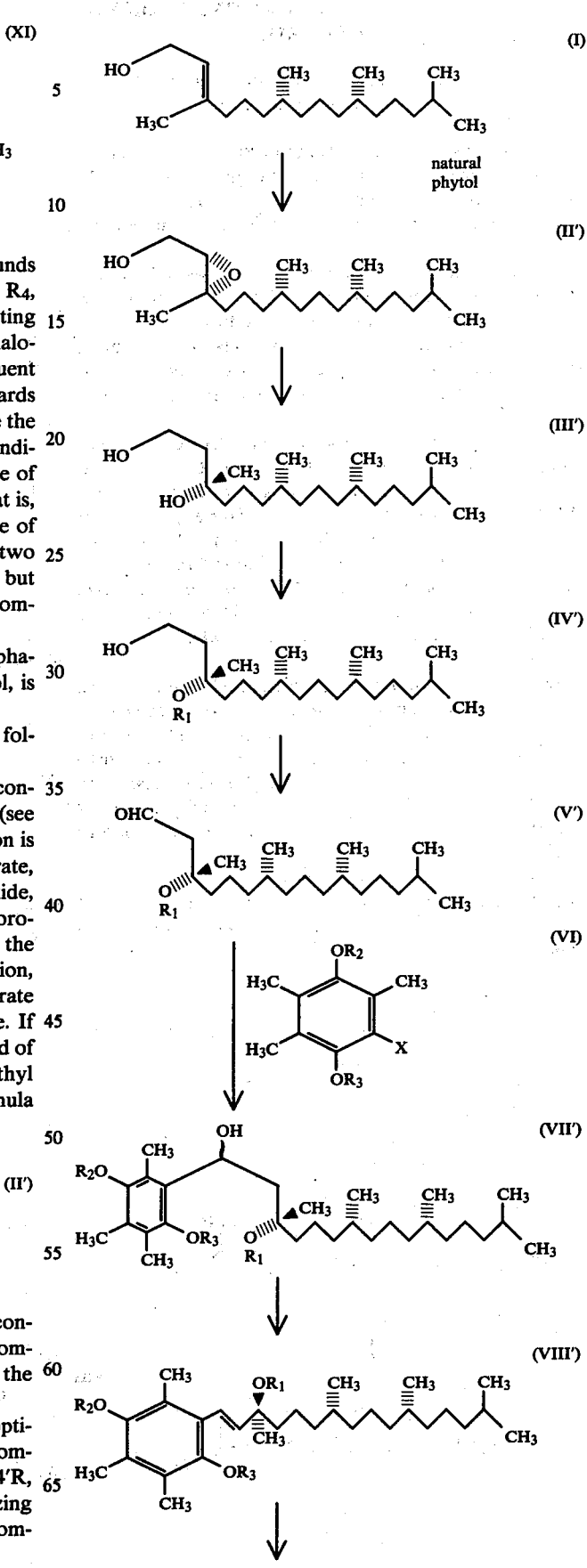

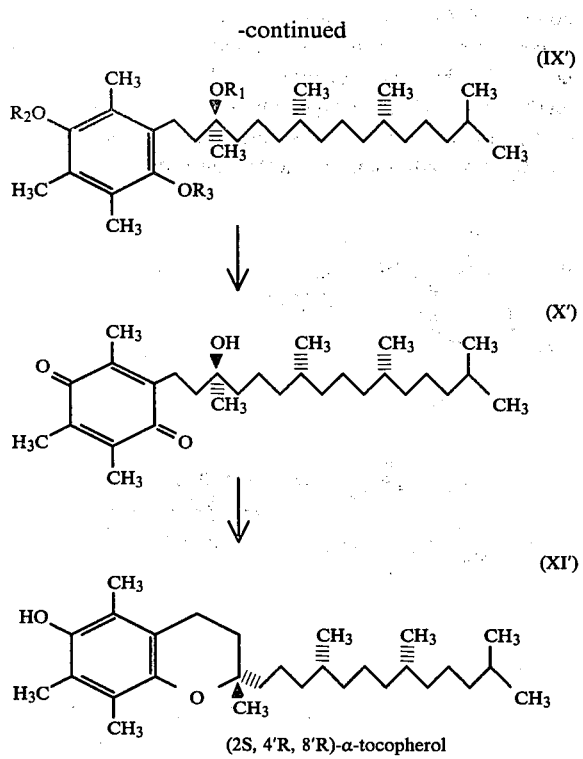

(2S, 4′R, 8′R)-α-tocopherol

The compound of formula (II) or (II′) is converted to the compound of formula (III) or (III′) by reductive cleavage of the epoxide. Among the conventional reducing agents usable in this reaction lithium aluminum hydride is preferred. In carrying out this reaction, an ether solvent, such as diethyl ether, tetrahydrofuran, etc., is used. The reaction temperature is not critical, but generally this reaction is carried out at a temperature in the range of from about −10° C. to about 40° C.

The compound of formula (III) or (III′) is converted to the compound of formula (V) or (V′) via the compound of formula (IV) or (IV′). First the 3-hydroxyl group is protected with a protecting group $R_1$, and then the 1-hydroxyl group is oxidized to form the aldehyde of formula (V) or (V′). In carrying out the formation of the compound of formula (IV) or (IV′), both the primary alcohol is protected, and the tertiary alcohol is protected. Then the protecting group of the primary alcohol is removed to afford the compound of formula (IV) or (IV′).

The compound of formula (IV) or (IV′) is converted to the compound of formula (V) or (V′) by oxidation. The entire reaction sequence is as illustrated below, first for the case of starting compound (III) and then for the case of starting compound (III′).

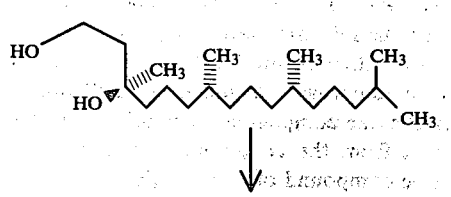

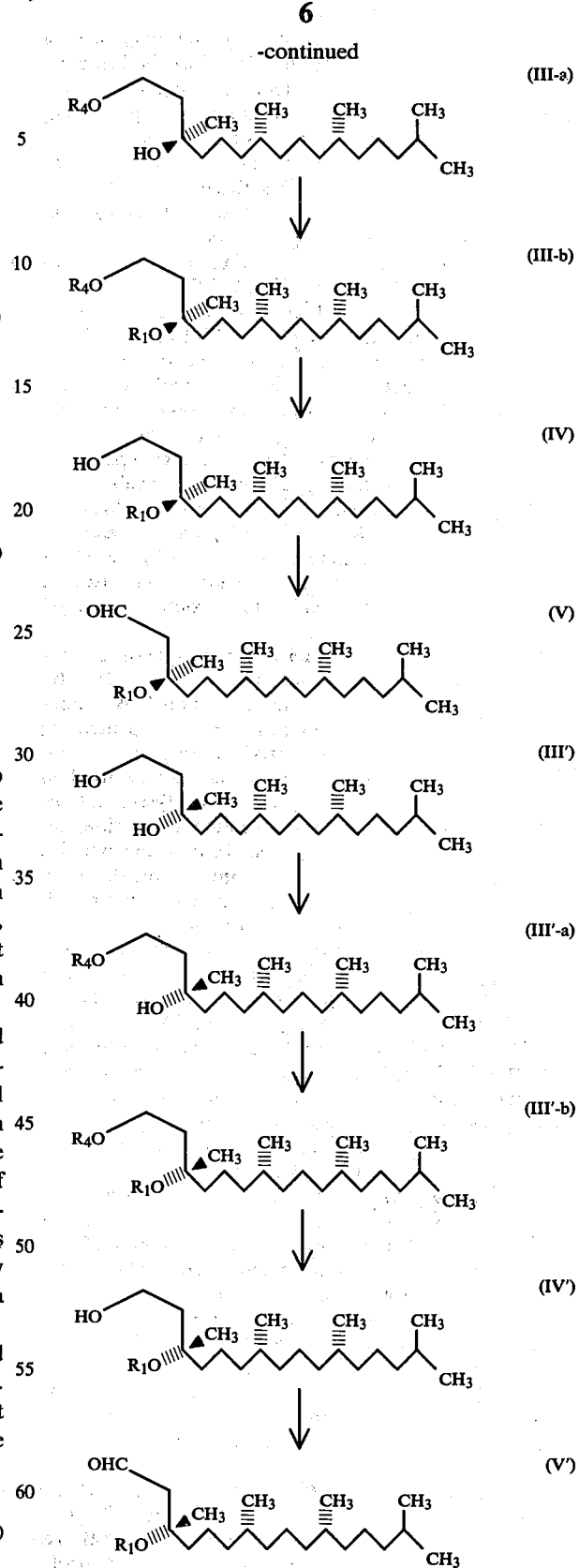

The compound of formula (III) or (III′) is converted to the compound of formula (III-a) or (III′-a) by protecting the primary alcohol with a protecting group which will react only with the primary alcohol. Any conventional protecting group reacting only with a primary alcohol can be utilized. Therefore, in the above structures, R₄ denotes a protecting group that reacts only with a primary alcohol. Among the protecting group reactants, ester derivatives such as acetyl chloride, propionyl chloride, butyroyl chloride and pivaloyl chloride are preferred. In using these carboxylic acid chlorides, the reaction conditions are not critical and the reaction is carried out in an amine solvent, such as pyridine, trimethylamine or triethylamine, at a temperature of from about 0° C. to about 70° C.

The compound of formula (III-a) or (III'-a) is converted to the compound of formula (III-b) or (III'-b) by protecting the tertiary alcohol. Any protecting group reactants that react with a tertiary alcohol can be utilized. Therefore, in the structures shown above, R₁ represents a protecting group that reacts only with a tertiary alcohol. Conventional protecting groups usable in the invention include alkyl, aryl, alkoxyalkyl and aralkyl groups. The preferred group for use in this reaction is methoxymethylene. In carrying out this reaction, a methoxymethylene halide, such as methoxymethylene chloride or methoxymethylene bromide, can be used, in a solvent of dichloromethane, dichloroethane, diethyl ether, or the like.

The compound of formula (III-b) or (III'-b) is converted to the compound of formula (IV) or (IV') by removing the protecting group in position 1. Any conventional method for reacting only with the protecting group in position 1 can be utilized. Among the conventional methods of saponification that can be used to remove the protecting group, basic hydrolysis reactions utilizing potassium hydroxide, sodium hydroxide, sodium carbonate, etc. can be used. In carrying out this reaction, the use of lithium aluminum hydride in an ether solvent is preferred, usable ethers including diethyl ether, tetrahydrofuran, and the like.

The compound of formula (IV) or (IV') is converted to the compound of formula (V) or (V') by oxidation of the primary alcohol to an aldehyde. In carrying out this reaction, chromic acid reagents, such as pyridinium chlorochromate (PCC) or Collins reagent (chromic anhydride-pyridine) can be utilized in a dichloromethane, dichloroethane or trichloroethane solvent, at a temperature of from about 0° C. to about 40° C.

The compound of formula (V) or (V') is converted to the compound of formula (VII) or (VII') by reaction with the compound of formula (VI). In the compound of formula (VI), X designates a halogen atom, such as chlorine, bromine and iodine. The compound of formula (VI) designates 1,4-protected 2-halo-3,5,6-trimethyl-1,4-hydroquinone. R₂ and R₃ are the same as for R₁ in the compound of formula (III-b) or (III'-b).

In carrying out this reaction, alkyl, aryl, alkoxyalkyl and aralkyl protecting groups can be used as R₂ and R₃. Among these, the preferred protecting group is methoxymethylene. The compound (VI) formed thereby is 2-halo-3,5,6-trimethyl 1,4-hydroquinone dimethoxymethyl ether.

The compound of formula (V) or (V') is converted to the compound of formula (VII) or (VII') by a Grignard reaction. In carrying out this reaction, the preferred solvents are ethers, such as diethyl ether, tetrahydrofuran, dioxane, etc. In carrying out the reaction, temperatures of from about 0°C. to about 50° C. are generally utilized.

The compound of formula (VI) is prepared as follows. 3,5,6-trimethyl-1,4-benzoquinone is converted to compound (VI) first by treatment with halogen, followed by reduction to afford a halogenated hydroquinone. The hydroxyl groups are then protected with methoxymethylene groups. The structure is illustrated in the case below wherein X designates bromide and R₂ and R₃ designate methoxymethylene groups.

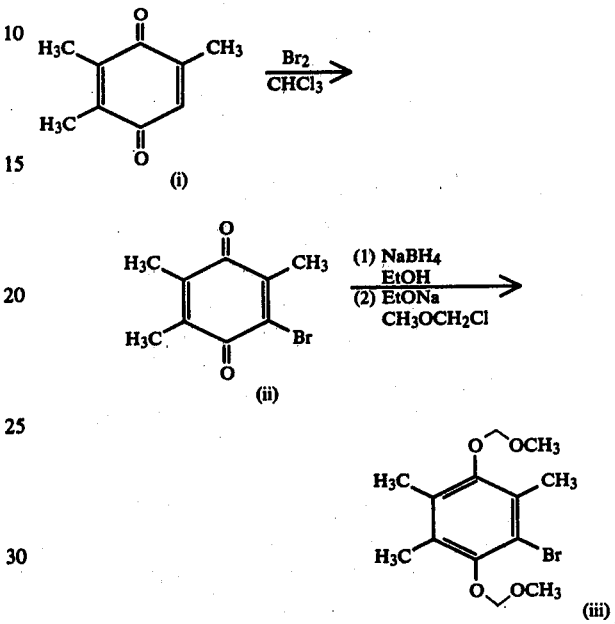

The compound of formula (VII) or (VII') is converted to the compound of formula (VIII) or (VIII') by dehydration. Any conventional dehydration method can be used for this purpose. Such conventional methods include chlorination by thionyl chloride to afford a chlorinated compound followed by dehydrochlorination with diazabicycloundecene (DBU) or diazabicyclononene (DBN). Any conventional inert solvent, such as diethyl ether, tetrahydrofuran, benzene or toluene, can be used for the chlorination. In carrying out this reaction, the temperature is not critical. Generally temperatures of from about 0° C. to about 50° C. are utilized. In carrying out the dehydrochlorination, inert solvents, such as dimethyl sulfoxide, benzene and toluene are used.

The compounds of formula (VIII) or (VIII') is converted to the compound of formula (IX) or (IX') by catalytic hydrogenation of the double bond on the aliphatic chain. Any conventional catalyst, such as palladium-charcoal, Raney nickel, platinum oxide, rhodium-aluminum, etc., can be used. In carrying out this reaction, temperatures of from about 0° C. to about 80° C. and solvents of ethanol, methanol, propanol, acetic acid, benzene, toluene, diethyl ether, etc., are utilized.

The compound of formula (IX) or (IX') is converted to the compound of formula (X) or (X') by removal of all of the protecting groups R₁, R₂ and R₃, followed by oxidation. In accordance with another embodiment of this invention, the compound of formula (x) or (X') can be prepared from the compound of formula (IX) or (IX') via the compound of formula (IX-a) or (IX'-a).

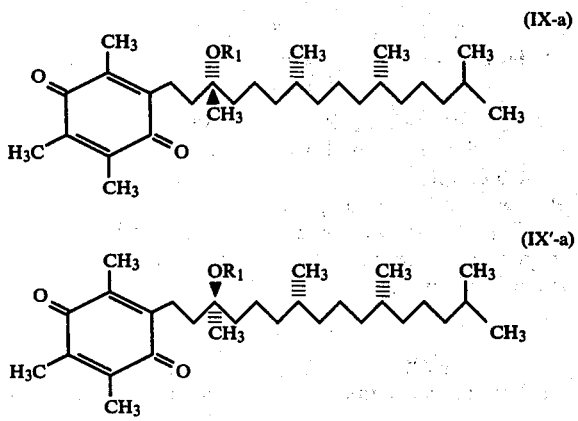

The compound of formula (IX-a) or (IX'-a) can be isolated, but such a step is not essential.

Any conventional method of removing the protecting groups can be utilized to form the compounds of formulas (X) and (X'). Among the preferred methods for removing the protecting groups are treatment with acetic acid, hydrochloric acid-methanol, sulfuric acid-methanol or palladium-charcoal in a hydrogen atmosphere. Any conventional method of converting hydroquinone to quinone can then be utilized to complete the reaction. Preferred oxidizing reagents include lead dioxide, silver oxide, hydrogen peroxide, Fremy's salt, etc.

The compound of formula (X) or (X') is converted to the compound of formula (XI) or (XI') by acidic cyclization to provide optically active alpha-tocopherol. Among the acids, d-camphor sulfonic acid is preferred. In carrying out this reaction, an inert solvent, such as methanol, ethanol, propanol, acetic acid and diethyl ether, is used, at a temperature of from about 0° C. to about 90° C., to provide optically active (2R, 4'R, 8'R) alpha-tocopherol. In carrying out this reaction, the procedure described in O. Isler et al, Helv. Chim. Acta. 50, 1168 (1967) can also be utilized.

(2R, 4'R, 8'R) alpha-tocopherol synthesized according to the invention was fully characterized physically and chemically by comparison with naturally occurring d-alpha-tocopherol. For instance, the $[\alpha]_D$ value of acetate of (2R, 4'R, 8'R) alpha-tocopherol synthesized according to the invention, and the oxidation product produced by treatment of (2R, 4'R, 8'R) alpha-tocopherol with potassium ferricyanide absolutely correspond with the results obtained using authentic natural tocopherol.

The following intermediates in this invention are novel compounds: (II), (II'), (III), (III'), (IV), (IV'), (V), (V'), (VII), (VII'), (VIII), (VIII'), (IX), (IX'), (III-a), (III'-a), (III-b), (III'-b), (IX-a) and (IX'-a).

The present invention is of great value because optical resolution is not absolutely necessary in order to produce optically active alpha-tocopherol by the process of the invention.

The following examples are illustrative of the invention, but the invention is not limited thereto.

EXAMPLE 1

Synthesis of (2S, 3S)-epoxy-(3S, 7R, 11R)-3,7,11,15-tetramethylhexadecane-1-ol (formula II')

A solution of 11.4 g (40 mM) of titanium tetraisopropoxide and 8.24 g (40 mM) of L-(+)-diethyl tartrate in 400 ml of dry dichloromethane was stirred at −20° C. to −30° C. in a nitrogen atmosphere. After stirring for 10 min., 12 g (40 mM) of natural phytol in 30 ml of dry dichloromethane was added and then a dichloroethane solution containing 80 mM of t-butyl hydroperoxide was added. The reaction was monitored by thin layer chromatography (tlc). (CHCl$_3$-benzene solvent).

After stirring for 2 hours at −20° C. to −30° C., 100 ml of 10% tartric acid solution was added and the drying bath was then removed. The organic layer was separated and washed with water. The dried organic solution was concentrated under water aspirator pressure to give 12.4 g of a colorless oil. This crude product was dissolved in 300 ml of diethyl ether and 120 ml of 1 N sodium hydroxide solution was added with ice cooling.

After stirring for 30 min., the organic layer was separated, washed with water and dried over magnesium sulfate. This diethyl ether solution was concentrated under water aspirator pressure to give 12.2 g of a colorless liquid. This crude material was chromatographed on 200 g of 60 to 80 mesh silica gel. Elution with n-hexane-ethyl acetate gave 11.7 g of the pure title compound (yield: 91.3%).

$[\alpha]_D^{25} = -4.4°$ (c 3.63 ETOH). Anal. Calcd. for C$_{20}$H$_{40}$O$_2$=C, 76.86%; H, 12.90%. Found: C, 77.14%; H, 12.75%. IR $v$cm$^{-1}$=3,400. NMR (CDCl$_3$) δ: 0.87 (d, 6H, J=6 Hz) 1.30 (s, 3H) 2.20 (m, 1H) 2.97 (d-d, 1H) 3.48–4.00 (m, 2H). MS m/e=294.

EXAMPLE 2

Synthesis of (2R, 3R)-epoxy-(3R, 7R, 11R)-3, 7, 11, 15-tetramethylhexadecane-1-ol (formula II)

5.7 g (20 mM of titanium tetraisopropoxide, 4.2 g (20 mM) of D-(−)-diethyl tartrate, 6 g (20 mM) of natural phytol and 40 mM) of t-butyl hydroperoxide were reacted in the same manner as in Example 1 to afford 5.6 g of the title compound (yield: 89.7%).

$[\alpha]_D^{25} = +4.3°$ (c 2.8 ETOH)

IR, NMR, Mass spectra were completely identical with the spectra obtained in Example 1.

EXAMPLE 3

Synthesis of (3S, 7R, 11R)-3, 7, 11, 15-tetramethylhexadecane-1,3-diol (formula III')

To a solution of 0.76 g (20 mM) of lithium aluminum hydride in 100 ml of THF was added 20 ml of a THF solution containing 6.24 g (20 mM) of (2S, 3S)-epoxy-(3S, 7R, 11R)-3, 7, 11, 15-tetramethylhexadecane-1-ol over a period of 30 min.

After stirring for 2 hours at 5° C., the reaction mixture was treated in the usual manner to give 6.1 g of the title compound (yield: 100%).

Anal. Calcd. for C$_{20}$H$_{42}$O$_2$: C, 76.37%; H, 13.46% Found: C, 76.10%; H, 13.57%. IR $v$cm$^{-1}$=3400. NMR (CDCl$_3$) δ: 0.86 (d, 6H, J=6 Hz), 1.24 (s, 3H) 2.40 (b-s, 1H), 2.84 (b-s, 1H), 3.65–4.00 (m, 2H), MS m/e: 296

EXAMPLE 4

Synthesis of (3R, 7R, 11R)-3, 7, 11, 15-tetramethylhexadecane-1,3-diol (formula III)

1.52 g (40 mM) of lithium aluminum hydride and 2.48 g (40 mM) of (2R, 3R)-epoxy-(3S, 7R, 11R)-3, 7, 11, 15-tetramethylhexadecane-1-ol were reacted in the same manner as in Example 3 to give 2.3 g (yield: 100%) of the title compound.

IR, NMR and Mass spectra were completely identical with the spectra obtained in Example 3.

EXAMPLE 5

Synthesis of (3S, 7R, 11R)-3, 7, 11, 15-tetramethyl-3-methoxymethyleneoxy-hexadecane-1-ol (formula IV')

(i)

To a solution of 6.3 g (20 mM) of (3S, 7R, 11R)-3, 7, 11, 15-tetramethylhexadecane-1,3-diol in 50 ml of pyridine was added 2.9 g of (24 mM) of pivaloyl chloride at 0° C.

After stirring for 1 hour, the reaction mixture was poured into 200 ml of 5% HCl solution. The organic layer was washed with water, then dried to give 7.7 g of crude material.

(ii)

To the solution of 7.7 g of pivaloyl ester in 100 ml of dry dichloromethane, 2.9 g (24 mM) of N,N-dimethyl aniline was added followed by addition of 1.9 g (24 mM) of methoxymethyl chloride.

After stirring for 4 hours at ambient temperature, the reaction mixture was poured into 100 ml of 5% HCL solution. Work-up with diethyl ether in the usual manner gave 8.2 g of colorless oil.

This material was chromatographed on 150 g of 60 to 80 mesh silica gel. Elution with n-hexane and ethyl acetate afforded 8.0 g of the pure compound (yield: 95%).

$[\alpha]_D^{25} = +2.13$ (c 6.34 ETOH). Anal. Calcd. for $C_{27}H_{54}O_4$; C, 73.25%; H, 12.30%; Found C, 73.86%; H, 12.45%; IR $\nu cm^{31\ 1} = 1745$. NMR ($CDCl_3$) δ: 0.86 (d, 6H, J=6 Hz) 1.20 (s, 9H), 1.24 (s, 3H), 1.85 (t, 2H, J=7 Hz), 3.37 (s, 3H), 4.16 (t, 2H, J=7 Hz), 4.70 (s, 2H). MS m/e=442.

(iii)

The solution of 8.0 g of the above compound produced in (ii) in 20 ml of diethyl ester was added to a solution of 1.0 g of lithium aluminum hydride in 50 ml of diethyl ether at 0° C.

After stirring for 1 hour, the reaction mixture was chilled with an ice bath. Work-up with water and 15% NaOH solution in the usual manner gave 6.5 g of the title compound (yield: 95%).

$[\alpha]_D^{25} = +1.8°$ (c 7.50 ETOH)

Anal. Calcd. for $C_{22}H_{46}O_3$: C, 73.74%; H, 12.93%; Found: C, 73.36%; H, 13.28%. IR $\nu cm^{-1} = 3450$. NMR ($CDCl_3$) δ: 0.86 (d, 6H, J-6 Hz), 1.28 (s, 3H), 2.80 (t, 1H, J=5 Hz), 3.28 (s, 3H), 3.78 (q, 2H, J=5 Hz), 4.72 (s, 2H). MS m/e=358, 340, 327.

EXAMPLE 6

Synthesis of (3R, 7R, 11R)-3, 7, 11, 15-tetramethyl-3-methoxymethleneoxyhexadecane-1-ol (formula IV)

6.3 g (20 mM) of (3R, 7R, 11R)-3, 7, 11, 15-tetramethylhexadecane-1,3-diol was treated in the same manner as in Example 5, (i), (ii) and (iii), to give 6.4 g (yield: 89.3%) of the title compound.

$[\alpha]_D^{25} = -1.8°$ (c 3.59 ETOH) IR, NMR and Mass spectra were completely identical with the spectra obtained in Example 5.

EXAMPLE 7

Synthesis of (3S, 7R, 11R)-3, 7, 11, 15-tetramethyl-3-methoxymethyleneoxyhexadecane-1-al (formula V')

To a solution of 3.6 g (10 mM) of (3S, 7R, 11R)-3, 7, 11, 15-tetramethyl-3-methoxymethyleneoxyhexadecane-1-ol in 50 ml of dichloromethane was added 6.4 g (30 mM) of PCC in small portions. The reaction was monitored by tlc.

After stirring for several hours at room temperature, 50 ml of diethyl ether was added to the reaction mixture and filtered through 50 g of Florisil. The resulting filtrate was evaporated to afford 3.7 g of yellow oil. This crude material was chromatographed on 70 g of 60 to 80 mesh silica gel. Elution with n-hexane and diethyl ether afforded 3.1 g of the colorless title compound (yield: 87.1%)

$[\alpha]_D^{25} = +6.66°$ (c 2.1 ETOH) Anal. Calcd. for $C_{22}H_{44}O_3$: C, 74.10%; H, 12.44%; Found: C. 73.89%; H. 12.73%, IR $\nu cm^{-1} = 1730$. NMR ($CDCl_3$) δ: 0.86 (d, 6H), 1.32 (s, 3H), 2.52 (t, 2H), 3.36 (s, 3H), 4.72 (s, 2H), 9.80–9.97 (m, 1H). MS m/e=356.

EXAMPLE 8

Synthesis of (3R, 7R, 11R)-3, 7, 11, 15-tetramethyl-3-methoxymethyleneoxyhexadecane-1-al (formula V)

5.4 g (15 mM) of (3R, 7R, 11R)-3, 7, 11, 15-tetramethyl-3-methoxymethyleneoxy hexadecane-1-ol and 9.6 g (45 mM) of PCC were reacted in the same manner as in Example 7 to give 4.8 g (yield: 89.7%) of the title compound $[\alpha]_D^{25} = -6.45°$ (c 2.17 ETOH)

IR, NMR and Mass spectra were completely identical with the spectra obtained in Example 7.

EXAMPLE 9

Synthesis of 2-[(3'S, 7'R, 11'R)-3', 7', 11', 15'-tetramethyl-3'-methoxymethyleneoxy-1'-hydroxy hexadecanyl]-3, 5, 6-trimethyl-1, 4-benzohydroquinone dimethoxymethyl ether (formula VII')

To a solution of 0.24 g (10 mM) of magnesium in 20 ml of dry THF was added 1 to 2 drops of ethylenedibromide for activation of the magnesium. To this solution was added 3.19 g (10 mM) of 2-bromo-3, 5, 6-trimethyl-1,4-hydroquinone dimethoxymethyl ether in 10 ml of dry THF. After the addition was finished, the reaction mixture was refluxed for 2 hours.

To this Grignard reagent was added 15 ml of dry THF solution containing 2.85 g (8 mM) of (3S, 7R, 11R)-3, 7, 11, 15-tetramethyl-3-methoxymethyleneoxy hexadecane-1-al. After stirring for 1 hour at reflux, the reaction mixture was poured into 100 ml of saturated NH₄Cl solution.

Work-up with diethyl ether in the usual manner gave 5.5 g of pale yellow oil.

This crude material was chromatographed on 100 g of 60 to 80 mesh silica gel. Elution with n-hexane and diethyl ether afforded 3.8 g of the colorless title compound (yield: 79.7%).

$[\alpha]_D^{25} = -4.58°$ (c 2.4 ETOH)

Anal. Calcd. for $C_{35}H_{64}O_7$: C, 70.43%; H, 10.81%, Found: C, 70.30%; H, 11.01%; IR $\nu cm^{-1} = 3500$. NMR (CDCl₃) δ: 0.86 (d, 6H, J=7 Hz), 2.18 (s, 3H), 2.20 (s, 3H), 2.42 (d, 3H, J=2 Hz), 3.40 (s, 3H), 3.63 (s, 6H), 3.76–3.96 (m, 1H), 4.75 (d, 2H, J=2 Hz), 4.86 (s, 2H), 4.96 (s, 2H), 5.28–5.57 (m, 1H).MS m/e=596.

EXAMPLE 10

Synthesis of 2-[(3'R, 7'R, 11'R)-3', 7', 11', 15'-tetramethyl-3'-methoxymethyleneoxy-1'-hydroxy hexadecanyl]-3, 5, 6-trimethyl-1, 4-benzohydroquinone dimethoxymethyl ether (formula VII)

0.12 g (5 mM) of magnesium, 1.6 g (5 mM) of 2-bromo-3, 5, 6-trimethyl-1,4-hydroquinone dimethoxymethyl ether and 1.4 g (4 mM) of (3R, 7R, 11R)-3, 7, 11, 15-tetramethyl-3-methoxymethyleneoxyhexadecane-1-al were reacted according to Example 9 to give 1.8 g (yield: 75.6%) of the colorless title compound.

$[\alpha]_D^{25} = +5.87°$ (c 5.14 ETOH)

IR, NMR and Mass spectra were completely identical with the spectra obtained in Example 9.

EXAMPLE 11

Synthesis of 2-[(3'S, 7'R, 11'R)-3', 7', 11', 15'-tetramethyl-3'-methoxymethyleneoxy-1'-hexadecenyl]-3, 5, 6-trimethyl-1,4-benzohydroquinone dimethoxymethyl ether (formula VIII')

To a solution of 1.8 g (3 mM) of 2-[(3'S, 7'R, 11'R)-3', 7', 11', 15'-tetramethyl-3'-methoxymethyleneoxy-1'-hydroxy hexadecanyl]-3,5,6-trimethyl-1, 4-benzohydroquinone dimetoxymethyl ether in 50 ml of ether were added successively 3 ml of pyridine and 1.0 g (8.4 mM) of thionyl chloride at 0° C.

After stirring for 30 min., the reaction mixture was poured into 50 ml of 5% HCl solution. Work-up with diethyl ether in the usual manner gave 1.9 g of crude product material.

The product did not show hydroxyl absorption in its IR spectrum.

1.9 g. of this crude material were dissolved in 30 ml of dry DMSO, and then treated with 2 g of DBN at 100° C.

After stirring for 30 min., the reaction mixture was poured into 100 ml of ice water. Work-up with diethyl ether in the usual manner gave 1.8 g of pale yellow oil. This material was chromatographed on 50 g of silica gel. Elution with n-hexane and diethyl ether afforded 1.5 g of the colorless title compound (yield: 86.4%)

$[\alpha]_D^{25} = -10.08°$ (c 7.8 ETOH) Anal. Calcd. for $C_{35}H_{62}O_6$: C, 72.62%; H, 10.80%, Found: C, 72.98%; H, 11.07%. NMR (CDCl₃) δ: 0.87 (d, 6H, J=7 Hz), 1.44 (s, 3H), 2.23 (s, 6H) 2.27 (s, 3H), 3.40 (s, 3H) 3.57 (s, 3H), 3.63 (s, 3H), 4.75 (q, 2H, J=6 Hz), 4.85 (s, 2H), 4.90 (s, 2H), 5.90 (d, 1H, J=17 Hz), 6.52 (d, 1H, J=17 Hz). MS m/e=578.

EXAMPLE 12

Synthesis of 2-[(3'R, 7'R, 11'R)-3', 7', 11', 15'-tetramethyl-3'-methoxymethyleneoxy-1'-hexadecenyl]-3, 5, 6-trimethyl-1,4-benzohydroquinone dimethoxymethyl ether (formula VIII)

1.2 g (2 mM) of 2-[(3'R, 7'R, 11'R)-3', 7', 11', 15'-tetramethyl-3'-methoxymethyleneoxy-1'-hydroxy hexadecanyl]-3, 5, 6-trimethyl-1,4-benzohydroquinone dimethoxymethyl ether, 0.67 g (5.6 mM) of thionyl chloride and 1.3 g of DBN were reacted according to Example 11 to give 0.9 g (yield: 77.8%) of the title compound.

$[\alpha]_D^{25} = +11.81°$ (c 2.07 ETOH)

IR, NMR and Mass spectra were completely identical with the spectra obtained in Example 11.

EXAMPLE 13

Synthesis of 2-[(3'S, 7'R, 11'R)-3', 7', 11', 15'-tetramethyl-3'-methoxymethyleneoxy hexadecanyl]-3, 5, 6-trimethyl-1,4-benzohydroquinone dimethoxymethyl ether (formula IX')

1.5 g (2.6 mM) of 2-[(3'S, 7'R, 11'R)-3', 7', 11', 15'-tetramethyl-3'-methoxymethyleneoxy-1'-hexadecenyl]-3, 5, 6-trimethyl-1, 4-benzohydroquinone dimethoxymethyl ether was dissolved in 50 ml of ethanol containing 500 mg of 5% palladium-charcoal. The resulting mixture was vigorously stirred under a hydrogen pressure of one atmosphere at room temperature.

After stirring for 2 hours, the reaction mixture was filtered. The filtrate was concentrated under aspirator pressure to give 1.45 g of the colorless title compound (yield: 100%)

$[\alpha]_D^{25} = -4.58°$ (c 3.5 ETOH)

Anal. Calcd. for $C_{35}H_{60}O_6$: C, 72.87%; H, 10.48%; Found: C, 73.15%; H, 10.65%. NMR (CDCl₃) δ: 0.87 (d, 6H, J=6 Hz), 2.20 (s, 6H), 2.25 (s, 3H), 2.52–2.84 (m, 2H), 3.40 (s, 3H), 3.62 (s, 6H), 4.76 (s, 2H), 4.88 (s, 2H) 4.89 (s, 2H). MS m/e=576

EXAMPLE 14

Synthesis of 2-[(3'R, 7'R, 11'R)-3', 7', 11', 15'-tetramethyl-3'-methoxymethyleneoxy hexadecanyl]-3, 5, 6-trimethyl-1,4-benzohydroquinone dimethoxymethyl ether (formula IX)

1.06 g (2 mM) of 2-[(3'R, 7'R, 11'R)-3', 7', 11', 15'-tetramethyl-3'-methoxymethyleneoxy-1'-hexadecenyl]-3, 5, 6-trimethyl-1, 4-benzohydroquinone dimethoxymethyl ether and 0.3 g of 5% palladium-charcoal were reacted according to Example 13 to give 1.04 g of the colorless title compound.

$[\alpha]_D^{25} = +5.02°$ (c 4.8 ETOH)

IR, NMR and Mass spectra were completely identical with the spectra obtained in Example 13.

EXAMPLE 15

Synthesis of 2-[(3'S, 7'R, 11'R)-3', 7', 11', 15'-tetramethyl-3'-hydroxyhexadecanyl]-3, 5, 6-trimethyl-1,4-benzoquinone, also called (alpha-(3'S)-tocopheryl quinone) (formula X')

(i)

To a solution of 1.45 g (2.5 mM) of 2-[(3'S, 7'R, 11'R)-3', 7', 11', 15'-tetramethyl-3'-methoxymethyleneoxy hexadecanyl]-3, 5, 6-trimethyl-1,4-benzohydroquinone dimethoxymethyl ether in 20 ml of THF was added 20 ml of 10% HCl solution. After stirring for 1 hour at room temperature, the reaction mixture was diluted with 50 ml of water. This solution was extracted with diethyl ether twice. To the combined ether solutions was added 2 g of lead dioxide at room temperature.

After stirring for 1 hour, the reaction mixture was filtered and the filtrate was concentrated under water aspirator pressure to give 1.4 g of pale yellow oil. This material was chromatographed on 30 g of silica gel. Elution with n-hexane and ether afforded 1.1 g (yield: 89.6%) of pale yellow alpha-(3'S)-methoxymethyl tocopheryl quinone.

$[\alpha]_D^{25} = -3.27°$ (c 1.69 ETOH)

Anal. Calcd. for $C_{31}H_{54}O_4$: C, 75.87%, H, 11.09%, Found: C, 76.18%; H, 11.36%. IR $\nu$ cm$^{-1}$=1640. NMR (CDCl$_3$) δ: 0.87 (d, 6H, J=6 Hz), 2.02 (s, 6H), 2.04 (s, 3H), 2.36-2.62 (m, 2H), 3.40 (s, 3H), 4.75 (s, 2H). MS m/e=429.

(ii)

To a solution of 1.1 g (2.2 mM) of alpha-(3'S)-methoxymethyl tocopheryl quinone in 30 ml of methanol was added 20 ml of 10% HCl solution.

After stirring for 5 hours at room temperature, 50 ml of water was added. This solution was extracted with 50 ml of diethyl ether twice. The combined ether solutions were concentrated under water aspirator pressure to give 1.1 g of pale red oil.

This material was chromatographed on 25 g of silica gel. Elution with n-hexane and diethyl ether afforded 0.9 g (yield: 89%) of the pale red title compound.

$[\alpha]_D^{25} = +1.08°$ (c 10.6 ETOH)

Anal. Calcd. for $C_{29}H_{50}O_3$: C, 77.97%; H, 11.28%. Found: C, 78.15%; H, 11.41%; IR $\nu$ cm$^{-1}$=3450, 1640. NMR (CDCl$_3$) δ: 0.87 (d, 6H, J=7 Hz), 1.24 (s, 3H), 2.00 (s, 6H), 2.03 (s, 3H), 2.44-2.70 (m, 2H). MS m/e=428.

EXAMPLE 16

Synthesis of 2-[(3'R, 7'R, 11'R)-3', 7', 11', 15'-tetramethyl-3'-hydroxy hexadecanyl]-3, 5, 6-trimethyl-1,4-benzoquinone, also called (alpha-(3'R)-tocopheryl quinone) (formula X)

(i)

1 g (1.7 mM) of 2-[(3'R, 7'R, 11'R)-3', 7', 11', 15'-tetramethyl-3'-methoxymethyleneoxy hexadecanyl]-3, 5, 6-trimethyl-1, 4-hydroquinone dimethoxymethyl ether, 15 ml of 10% HCl solution and 1.5 g of lead dioxide were reacted according to Example 15(i) to give 0.75 g (yield: 89.9%) of pale yellow alpha-(3'R)-methoxymethyl tocopheryl quinone.

$[\alpha]_D^{25} = +3.8°$ (c 4.39 ETOH)

IR, NMR and Mass spectra were completely identical with the spectra obtained in Example 15.

(ii)

0.75 g (1.5 mM) of alpha-(3'R)-methoxymethyl tocopheryl quinone and 15 ml of 10% HCl solution were reacted according to Example 15 (ii) to give 0.6 g (yield: 89.5%) of the pale red title compound.

$[\alpha]_D^{25} = -1.01°$ (c 18.8 ETOH)

IR, NMR and Mass spectra were completely identical with the spectra obtained in Example 15.

EXAMPLE 17

Synthesis of (2S, 4'R, 8'R)-alpha-tocopherol (formula XI')

1 g (4 mM) of d-camphor sulfonic acid was added to a solution of 0.9 g (2 mM) of 2-[(3'S, 7'R, 11'R)-3', 7', 11', 15'-tetramethyl-3'-hydroxy hexadecanyl]-3, 5, 6-trimethyl-1,4-benzoquinone in 20 ml of methanol. After stirring for 15 min. at room temperature, the mixture was poured into 50 ml of ice water. Work-up in the usual manner (extraction with diethyl ether 2 times, and drying over magnesium sulfate) afforded 0.85 g of pale yellow oil.

This material was chromatographed on 30 g of silica gel. Elution with n-hexane and diethyl ether afforded 0.8 g (yield: 93%) of colorless title compound.

$[\alpha]_D^{25} = +0.85°$ (c 1.15, benzene)

K$_3$Fe(CN)$_6$ oxidation product:

$[\alpha]_D^{25} = -29.6°$ (c 1.70, isooctane)

This (2S, 4'R, 8'R)-alpha-tocopheryl quinone was acetylated with acetic anhydride and pyridine to give (2S, 4'R, 8'R)-alpha-tocopheryl acetate in quantitative yield.

$[\alpha]_D^{25} = -2.25°$ (c 1.1 ETOH)

EXAMPLE 18

Synthesis of (2R, 4'R, 8'R)-alpha-tocopherol (formula XI)

0.65 g (2.6 mM) of d-camphor sulfonic acid and 0.6 g (1.3 mM) of 2-[(3'R, 7'R, 11'R)-3', 7', 11', 15'-tetramethyl-3'-hydroxy hexadecanyl]-3,5,6-trimethyl-1,4-benzoquinone were reacted according to Example 17 to give 0.52 g of the colorless title compound (yield: 90.3%)

$[\alpha]_D^{25} = -2.76°$ (c 1.07, benzene)

UV λ max=292 nm; $\epsilon_{cm}^{1\%} = 69.7$

K$_3$Fe(CN)$_6$ oxidation product:

$[\alpha]_D^{25} = +29.8°$ (c 1.05 isooctane)

Acetate (formed according to Example 17):

$[\alpha]_D^{25} = +3.49°$ (c 1.1 ETOH)

The embodiments of the invention in which an exclusive property or privilege is claimed are defined as follows:

1. A process for preparing an optically active alpha-tocopherol of the formula wherein A is $\equiv\!\!\!\begin{array}{c}\\CH_2-\\CH_3\end{array}$ or $\begin{array}{c}\\CH_2-\\CH_3\end{array}$, starting with an optically active compound of the formula

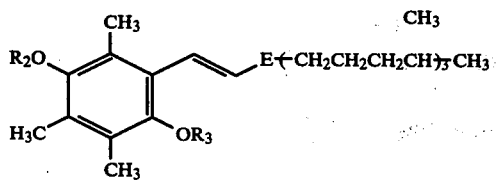

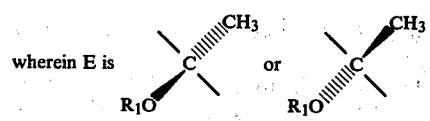

wherein E is and $R_1$, $R_2$ and $R_3$ are protecting groups for hydroxyl functions which comprises
  (1) catalytically hydrogenating the double bond in the aliphatic chain of the starting compound to form an optically active compound of the formula

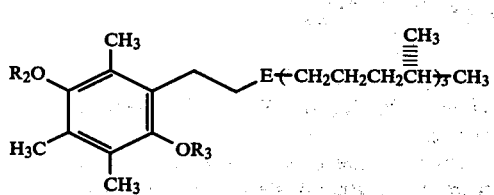

wherein E, $R_2$ and $R_3$ are the same as defined above,
  (2) removing the protecting groups $R_1$, $R_2$ and $R_3$ from the product of step (1) and then treating same with an oxidizing agent to form an optically active compound of the formula

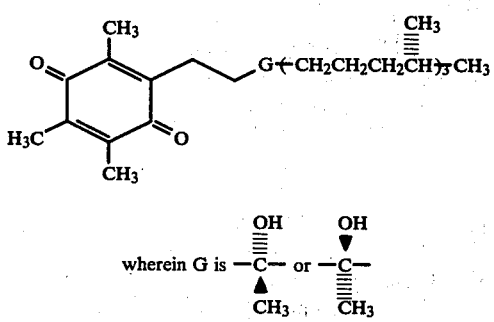

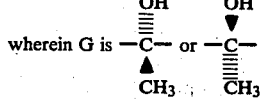

wherein G is and
  (3) effecting cyclization of the product of step (2) to obtain said optically active alpha-tocopherol.

2. A process for preparing an optically active alpha-tocopherol of the formula

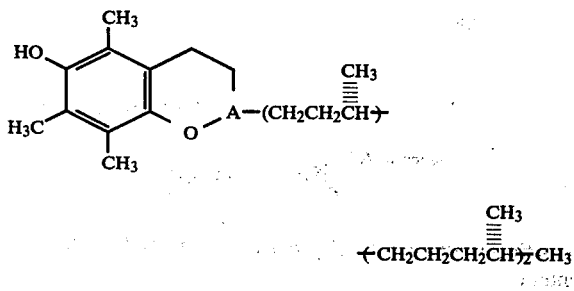

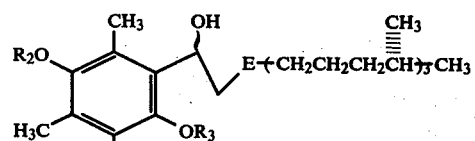

wherein A is starting with an optically active compound of the formula

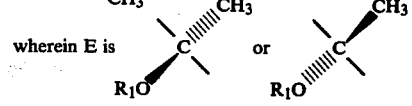

wherein E is and $R_1$, $R_2$ and $R_3$ are protecting groups for hydroxyl functions which comprises the steps of
  (1) converting the starting compound to form an optically active compound of the formula

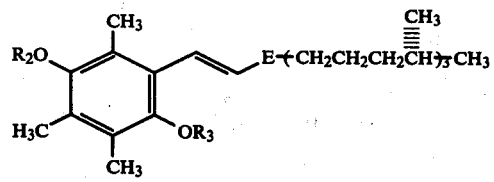

wherein E, $R_2$ and $R_3$ are the same as defined above,
  (2) catalytically hydrogenating the double bond in the aliphatic chain of the product of step (1) to form an optically active compound of the formula

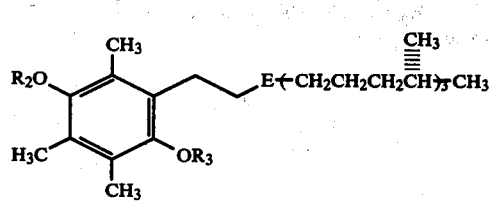

wherein E, $R_2$ and $R_3$ are the same as defined above,
  (3) removing the protecting groups $R_1$, $R_2$ and $R_3$ from the product of step (2) and then treating same with an oxidizing agent to form an optically active compound of the formula

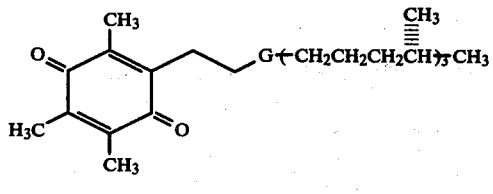

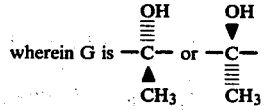

wherein G is and
(4) effecting cyclization of the product of step (3) to obtain said optically active alphatocopherol.

3. A process for preparing an optically active alpha-tocopherol of the formula

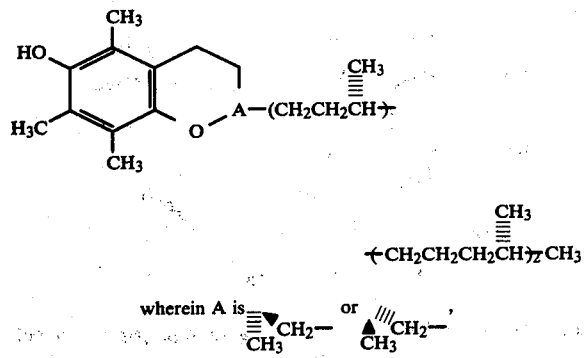

wherein A is 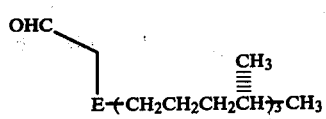

starting with an optically active compound of the formula

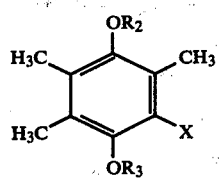

wherein E is 

and $R_1$ is a protecting group for a hydroxyl function which comprises the steps of
(1) reacting the starting compound with a compound of the formula

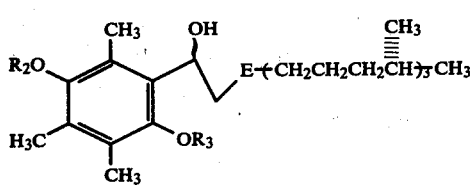

wherein $R_2$ and $R_3$ are protecting groups for hydroxyl functions and X is halogen,
to form an optically active compound of the formula

wherein E, $R_2$ and $R_3$ are the same as defined above,
(2) converting the product of step (1) to form an optically active compound of the formula

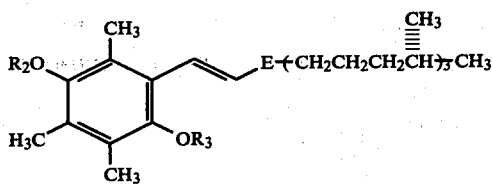

wherein E, $R_2$ and $R_3$ are the same as defined above,
(3) catalytically hydrogenating the double bond in the aliphatic chain of the product of step (2) to form an optically active compound of the formula

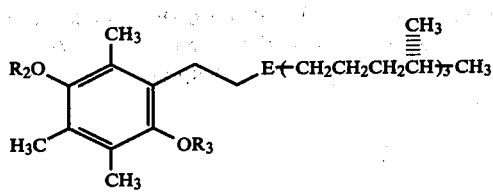

wherein E, $R_2$ and $R_3$ are the same as defined above,
(4) removing the protecting groups $R_1$, $R_2$ and $R_3$ from the product of step (3) and then treating same with an oxidizing agent to form an optically active compound of the formula

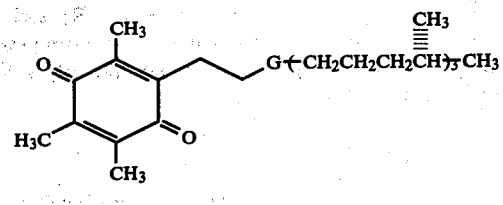

wherein G is 

and
(5) effecting cyclization of the product of step (4) to obtain said optically active alpha-tocopherol.

4. A process for preparing an optically active alpha-tocopherol of the formula

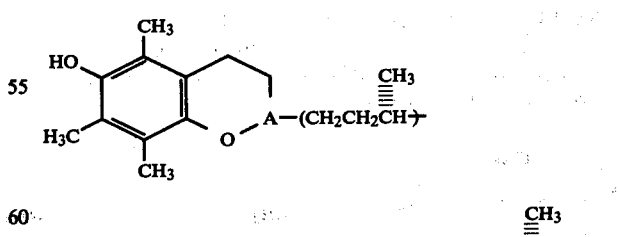

wherein A is 

starting with an optically active compound of the formula

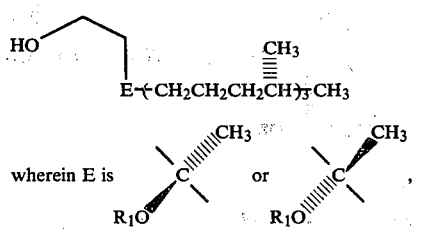

wherein E is 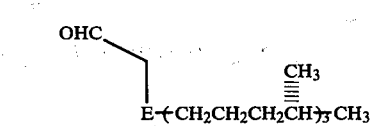

and R₁ is a protecting group for a hydroxyl function, which comprises the steps of (1) treating the starting compound with an oxidizing agent to form an optically active compound of the formula

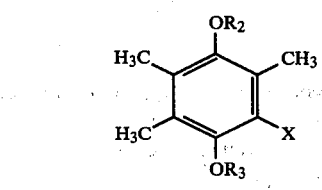

wherein E is the same as defined above, (2) reacting the product of step (1) with a compound of the formula

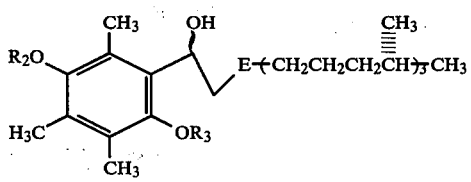

wherein R₂ and R₃ are protecting groups for hydroxyl functions and X is halogen, to form an optically active compound of the formula

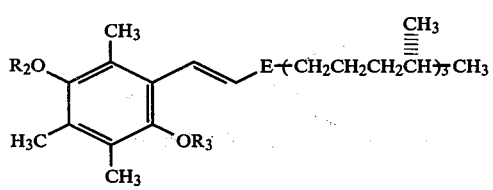

wherein E, R₂ and R₃ are the same as defined above, (3) converting the product of step (2) to form an optically active compound of the formula

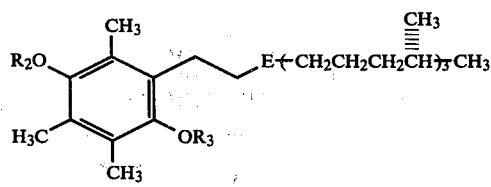

wherein E, R₂ and R₃ are the same as defined above, (4) catalytically hydrogenating the double bond in the aliphatic chain of the product of step (3) to form an optically active compound of the formula

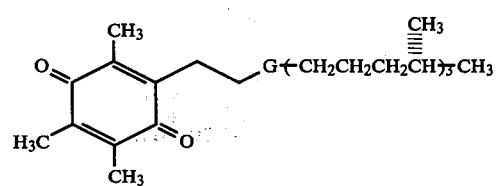

wherein E, R₂ and R₃ are the same as defined above, (5) removing the protecting groups R₁, R₂ and R₃ from the product of step (4) and then treating same with an oxidizing agent to form an optically active compound of the formula

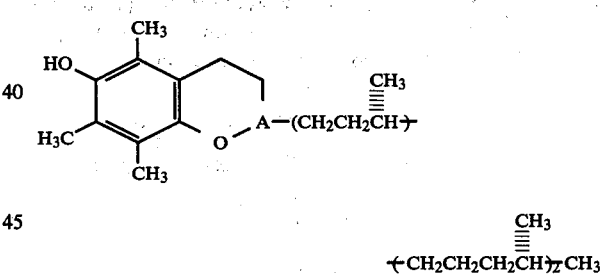

wherein G is 

and (6) effecting cyclization of the product of step (5) to obtain said optically active alpha-tocopherol.

5. A process for preparing an optically active alpha-tocopherol of the formula

wherein A is 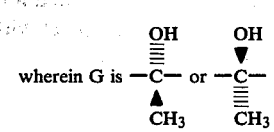, starting with an optically active compound of the formula

wherein D is which comprises the steps of (1) converting the starting compound to form an optically active compound of the formula

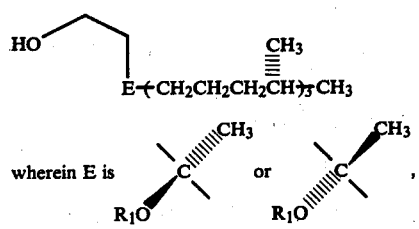

wherein E is and $R_1$ is a protecting group for a hydroxyl function, (2) treating the product of step (1) with an oxidizing agent to form an optically active compound of the formula

wherein E is the same as defined above, (3) reacting the product of step (2) with a compound of the formula

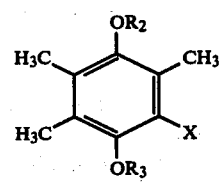

wherein $R_2$ and $R_3$ are protecting groups for hydroxyl functions and X is halogen, to form an optically active compound of the formula

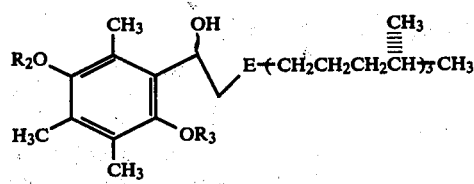

wherein E, $R_2$ and $R_3$ are the same as defined above, (4) converting the product of step (3) to form an optically active compound of the formula

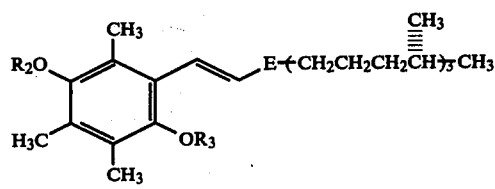

wherein E, $R_2$ and $R_3$ are the same as defined above, (5) catalytically hydrogenating the double bond in the aliphatic chain of the product of step (4) to form an optically active compound of the formula

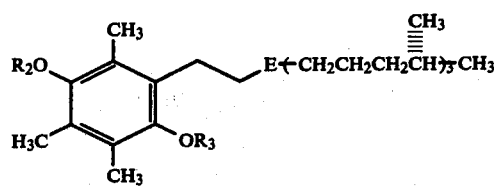

wherein E, $R_2$ and $R_3$ are the same as defined above, (6) removing the protecting groups $R_1$, $R_2$ and $R_3$ from the product of step (5) and then treating same with an oxidizing agent to form an optically active compound of the formula

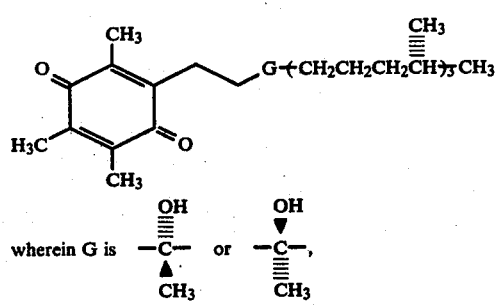

and (7) effecting cyclization of the product of step (6) to obtain said optically active alpha-tocopherol.

6. A process for preparing an optically active alpha-tocopherol of the formula

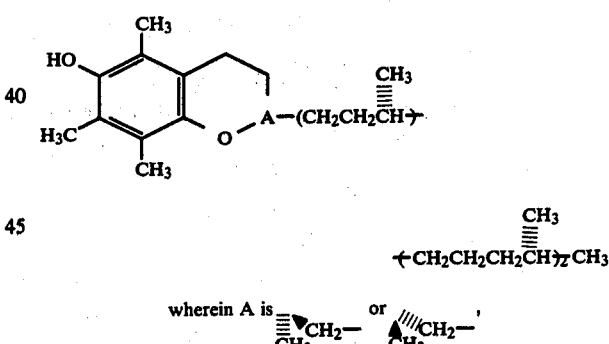

starting with an optically active compound of the formula

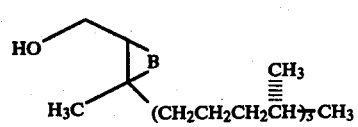

wherein B is which comprises the steps of
(1) treating the starting material with a reducing agent to form an optically active compound of the formula

wherein D is 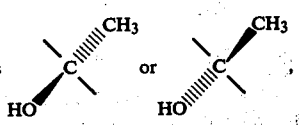, (2) converting the product of step (1) to form an optically active compound of the formula

wherein E is 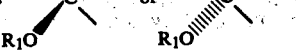, and $R_1$ is a protecting group for a hydroxyl function, (3) treating the product of step (2) with an oxidizing agent to form an optically active compound of the formula

wherein E is the same as defined above, (4) reacting the product of step (3) with a compound of the formula

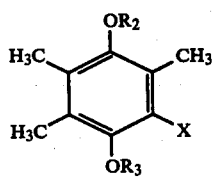

wherein $R_2$ and $R_3$ are protecting groups for hydroxyl functions and X is halogen, to form an optically active compound of the formula

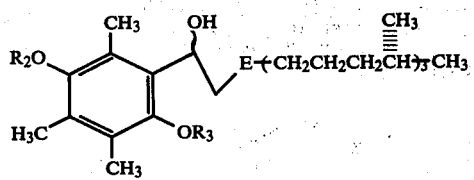

wherein E, $R_2$ and $R_3$ are the same as defined above, (5) converting the product of step (4) to form an optically active compound of the formula

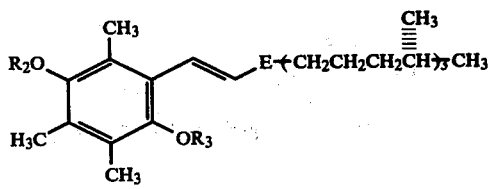

wherein E, $R_2$ and $R_3$ are the same as defined above, (6) catalytically hydrogenating the double bond in the aliphatic chain of the product of step (5) to form an optically active compound of the formula

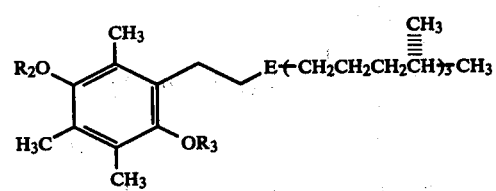

wherein E, $R_2$ and $R_3$ are the same as defined above, (7) removing the protecting groups $R_1$, $R_2$ and $R_3$ from the product of step (6) and then treating same with an oxidizing agent to form an optically active compound of the formula

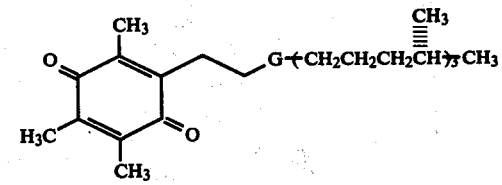

wherein G is 

and
(8) effecting cyclization of the product of step (7) to obtain said optically active alpha-tocopherol.

7. A process for preparing an optically active alpha-tocopherol of the formula

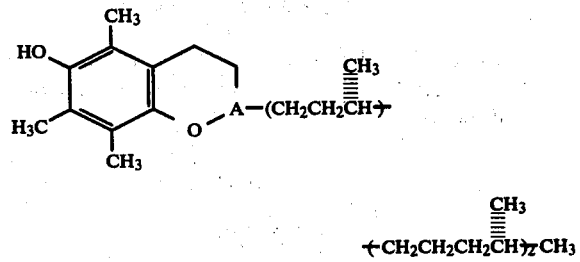

wherein A is 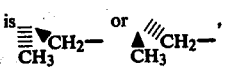, which comprises
(1) transforming phytol to an optically active compound of the formula

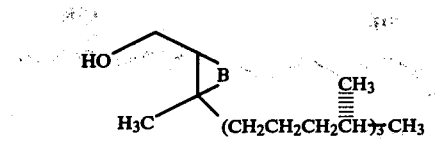

wherein B is ▲O or ⫽O, (2) treating the product of step (1) with a reducing agent to form an optically active compound of the formula

wherein D is (3) converting the product of step (2) to form an optically active compound of the formula

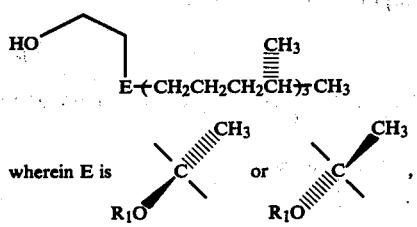

wherein E is and $R_1$ is a protecting group for a hydroxyl function, (4) treating the product of step (3) with an oxidizing agent to form an optically active compound of the formula

wherein E is the same as defined above, (5) reacting the product of step (4) with a compound of the formula

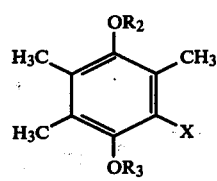

wherein $R_2$ and $R_3$ are protecting groups for hydroxyl functions and X is halogen, to form an optically active compound of the formula

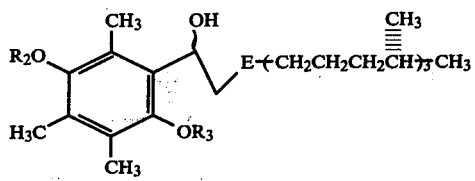

wherein E, $R_2$ and $R_3$ are the same as defined above, (6) converting the product of step (5) to form an optically active compound of the formula

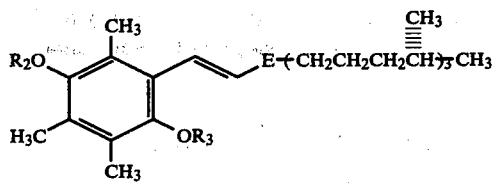

wherein E, $R_2$ and $R_3$ are the same as defined above, (7) catalytically hydrogenating the double bond in the aliphatic chain of the product of step (6) to form an optically active compound of the formula

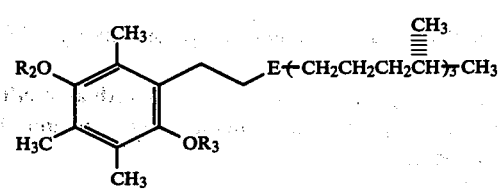

wherein E, $R_2$ and $R_3$ are the same as defined above, (8) removing the protecting groups $R_1$, $R_2$ and $R_3$ from the product of step (7) and then treating same with an oxidizing agent to form an optically active compound of the formula

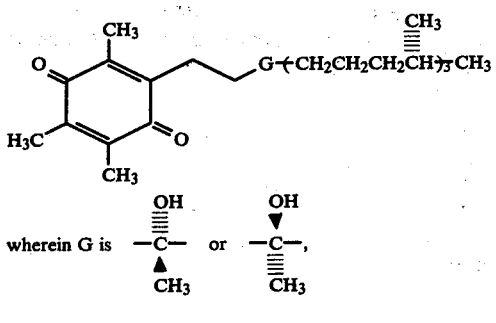

wherein G is and (9) effecting cyclization of the product of step (8) to obtain said optically active alphatocopherol.

8. A process which comprises effecting enantioselective oxidation of phytol by adding phytol to a solution of a tartrate ester and titanium tetraisopropoxide in a halogenated hydrocarbon solvent and then adding t-butyl hydroperoxide, under conditions effective to transform said phytol to an optically active compound of the formula

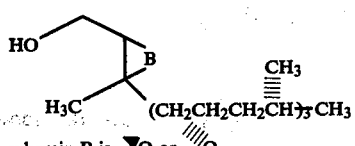

wherein B is ▲O or ⫽O.

* * * * *

UNITED STATES PATENT AND TRADEMARK OFFICE
CERTIFICATE OF CORRECTION

PATENT NO. : 4,433,159

DATED : February 21, 1984

INVENTOR(S) : Kimio Hamamura et al

It is certified that error appears in the above-identified patent and that said Letters Patent is hereby corrected as shown below:

Column 17, line 1; change the righthand portion of the formula to read as follows:

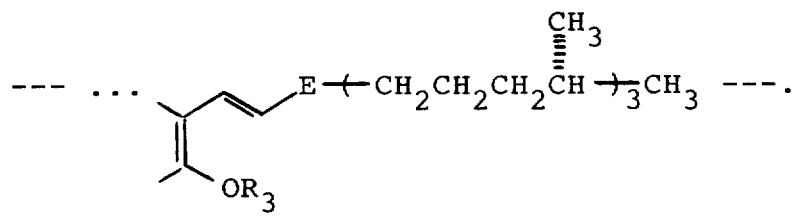

Signed and Sealed this

Fourth Day of September 1984

[SEAL]

Attest:

Attesting Officer

GERALD J. MOSSINGHOFF

Commissioner of Patents and Trademarks